United States Patent
Parks, II et al.

(10) Patent No.: US 9,068,933 B2
(45) Date of Patent: Jun. 30, 2015

(54) EGR DISTRIBUTION AND FLUCTUATION PROBE BASED ON CO2 MEASUREMENTS

(71) Applicant: UT-Battelle LLC, Oak Ridge, TN (US)

(72) Inventors: James E. Parks, II, Knoxville, TN (US);
William P. Partridge, Jr., Oak Ridge, TN (US); Ji Hyung Yoo, Williamsville, NY (US)

(73) Assignee: UT-Battelle, LLC, Oak Ridge, TN (US)

( * ) Notice: Subject to any disclaimer, the term of this patent is extended or adjusted under 35 U.S.C. 154(b) by 46 days.

(21) Appl. No.: 14/051,788

(22) Filed: Oct. 11, 2013

(65) Prior Publication Data
US 2014/0034833 A1 Feb. 6, 2014

Related U.S. Application Data

(63) Continuation-in-part of application No. 13/912,462, filed on Jun. 7, 2013.

(60) Provisional application No. 61/657,205, filed on Jun. 8, 2012.

(51) Int. Cl.
*G01N 21/35* (2014.01)
*G01N 21/3504* (2014.01)

(52) U.S. Cl.
CPC .................................. *G01N 21/3504* (2013.01)

(58) Field of Classification Search
CPC ............................ G01N 21/35; G01N 21/3504
USPC .................... 250/341.2, 343; 356/436, 437
See application file for complete search history.

(56) References Cited

U.S. PATENT DOCUMENTS

| 5,373,367 A | 12/1994 | DeGunther et al. |
| 5,751,423 A | 5/1998 | Traina et al. |

(Continued)

FOREIGN PATENT DOCUMENTS

JP 5898652 6/1983

OTHER PUBLICATIONS

Michael Cundy, Torsten Schucht, Olaf Thiele, and Volker Sick, High-speed laser-induced fluorescence and spark plug absorption sensor diagnostics for mixing and combustion studies in engines, Applied Optics, vol. 48, No. 4 / Feb. 1, 2009.

(Continued)

*Primary Examiner* — Mark R Gaworecki
(74) *Attorney, Agent, or Firm* — Warner Norcross & Judd LLP

(57) ABSTRACT

A diagnostic system having a laser, an EGR probe, a detector and a processor. The laser may be a swept-$\lambda$ laser having a sweep range including a significant $CO_2$ feature and substantially zero absorption regions. The sweep range may extend from about 2.708 μm to about 2.7085 μm. The processor may determine $CO_2$ concentration as a function of the detector output signal. The processor may normalize the output signal as a function of the zero absorption regions. The system may include a plurality of EGR probes receiving light from a single laser. The system may include a separate detector for each probe. Alternatively, the system may combine the light returning from the different probes into a composite beam that is measured by a single detector. A unique modulation characteristic may be introduced into each light beam before combination so that the processor can discriminate between them in the composite beam.

19 Claims, 12 Drawing Sheets

(56) References Cited

U.S. PATENT DOCUMENTS

| | | |
|---|---|---|
| 5,831,730 A | 11/1998 | Traina et al. |
| 5,999,257 A | 12/1999 | Myers et al. |
| 6,744,059 B2 | 6/2004 | DiDomenico et al. |
| 6,744,516 B2 | 6/2004 | DiDomenico et al. |
| 6,833,922 B2 | 12/2004 | DiDomenico et al. |
| 7,301,641 B1 | 11/2007 | Overby et al. |
| 7,839,492 B2 | 11/2010 | Parks, II et al. |
| 2007/0131882 A1* | 6/2007 | Richman ........................ 250/573 |

OTHER PUBLICATIONS

C. Schulz "Advanced laser imaging diagnostics in combustion," Z. Phys. Chem. 219, 509-554 (2005).

* cited by examiner

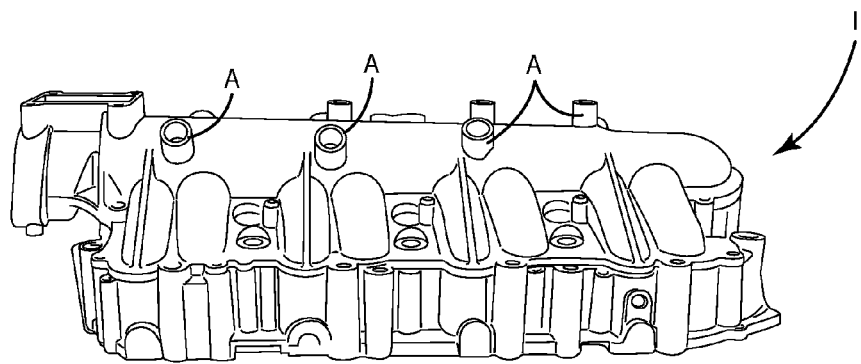
Fig. 9
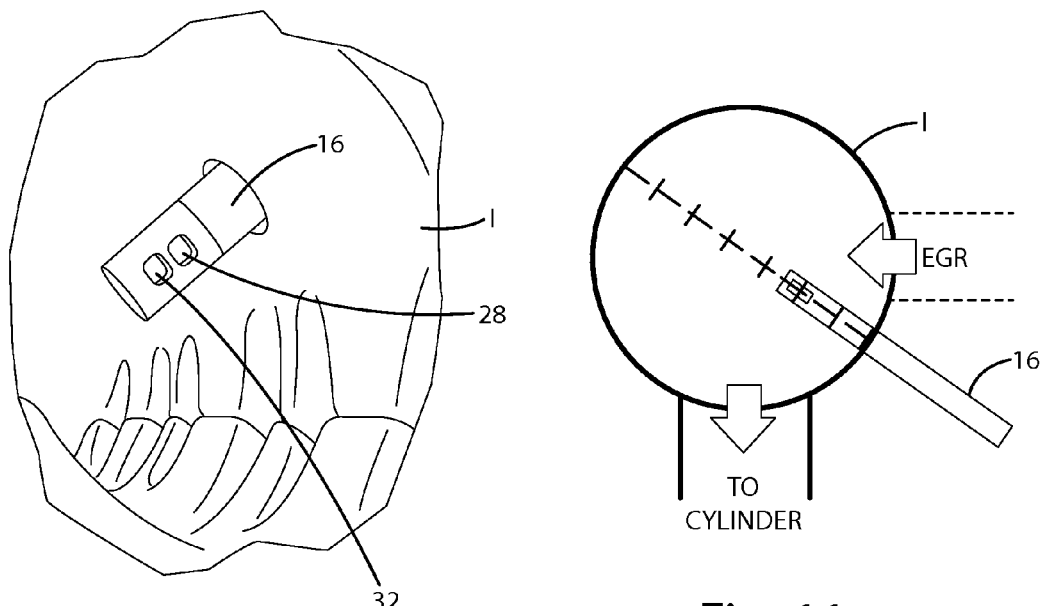
Fig. 10
Fig. 11

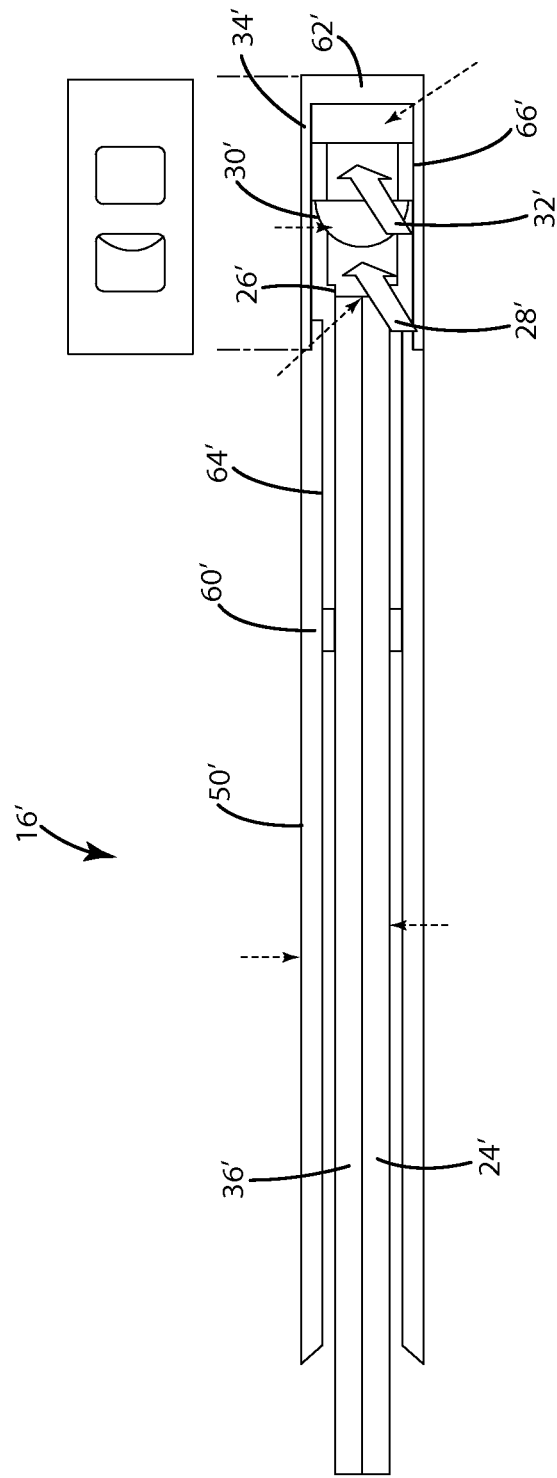

MULTIPLEX DETECTION EXPERIMENTAL SET-UP

SCHEMATIC OF SIGNAL PRE- AND POST- CONDITIONING
FOR MULTIPLEXED DETECTION

EGR DISTRIBUTION AND FLUCTUATION PROBE BASED ON CO2 MEASUREMENTS

CROSS REFERENCE TO RELATED APPLICATIONS

This application is a continuation-in-part of U.S. application Ser. No. 13/912,462, entitled EGR DISTRIBUTION AND FLUCTUATION PROBE BASED ON $CO_2$ MEASUREMENTS, filed Jun. 7, 2013, by Parks et al, which claims the benefit of U.S. Provisional Application No. 61/657,205, filed Jun. 8, 2012. U.S. Provisional Application No. 61/657,205 is incorporated herein by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND OF THE INVENTION

The present invention relates to internal combustion engine diagnostics and more specifically to apparatuses and methods for determining the spatial and temporal nonuniformities of $CO_2$ in an intake fluid stream.

Internal combustion engines typically suffer from the ability to produce undesirable $NO_X$ emissions. Experience has revealed that more $NO_X$ emissions are formed at higher combustion temperatures and that $NO_X$ formation has a nonlinear dependence on temperature. More specifically, lowering the combustion temperature a little can result in relatively large reductions in $NO_X$ formation.

Exhaust-gas recirculation, EGR, is a technology used to reduce automotive $NO_X$ emissions, and which involves mixing some of the engine exhaust with the intake air. The exhaust gas acts as a diluent in the inlet air that reduces peak combustion temperature. Ideally, the air/exhaust mixture, or EGR fraction, is uniform across the various cylinders of a multi-cylinder engine. However, practically the EGR fraction can vary from cylinder to cylinder and cycle to cycle due to various spatial and temporal nonuniformities; e.g., non-ideal mixing, intake-manifold restrictions, and overlap of valve events with manifold resonating. Such nonuniformities can cause one cylinder to reach a limit (e.g., incomplete combustion, etc.) earlier than the other cylinders, and can limit the performance of the other cylinders. Ultimately, the result is lost efficiency and increased engine emissions.

An EGR probe that can be used to identify non-uniformities, track their origins and assess mitigation strategies could be a powerful tool for optimizing efficiency and performance of multi-cylinder engines. For example, a probe of this nature may be capable of identifying spatial or temporal fluctuations in the performance of the EGR system, which may result from the design or configuration of the EGR system, the intake manifold, engine events or other factors.

In the past, EGR probes that rely on capillary action have been developed to assist in mapping $CO_2$ variations within an engine intake manifold. These tiny capillary probes allow samples to be extracted from the intake manifold and delivered to remote equipment for analysis. The capillary probes are capable of being spatially translated so that they can take samples from different location within the exhaust manifold. For example, the capillary probes are capable of being mounted in different apertures in the intake manifold and of being inserted to different depths within a given aperture. The samples extracted using capillary probes are analyzed remotely using absorption spectroscopy or mass spectrometry, or other analytical technique, to determine $CO_2$ concentration. Although a meaningful advance, conventional capillary probes suffer from a variety of disadvantages. Perhaps most notably, capillary-probe-based diagnostic systems are not fast enough to measure fast valve-time scale, crank-angle resolved variations. As a result, the use of capillary probes can place significant limitations on the capabilities the diagnostic system.

Another technique previously used to measure EGR fraction variations by cylinder is the use of oxygen sensors. Exhaust oxygen sensors are common on engines for vehicles and aid the engine system in controlling the air-to-fuel ratio during combustion. They function based on a solid state electrochemical cell (normally composed of a metal oxide). For the application of measuring EGR fraction distribution, they have limitations related to diffusion, temperature, and pressure. Gas measurement required diffusion into the electrochemical cell and also through a protective porous housing (commonly ceramic based); the time required for the diffusion process can limit temporal response especially relative to rapid cylinder-to-cylinder and cycle-to-cycle time scales. Also, the oxygen sensors must be heated to work effectively, and cool intake gas temperatures pose problems for the sensors to maintain the necessary sensor temperature. Lastly, variations in pressure in the intake system (often occurring especially for boosted engines) can alter oxygen sensor measurements.

SUMMARY OF THE INVENTION

The present invention provides an EGR probe capable of providing rapid and accurate measurement of $CO_2$ concentrations in a fluid stream, such as an engine intake manifold, intake runner or engine exhaust manifold. In one embodiment, the EGR probe is operatively coupled with a combined light source (a signal light source and a reference light source), a detector and a processor to provide a diagnostic system. The EGR probe of this embodiment includes a pitch optical cable (e.g., a hollow wave guide) that receives the light beam from the combined light source, a lens for focusing the light beam, a sampling chamber where the light beam passes through the fluid stream and a catch optical cable for conveying the light beam to the detector after it has passed through the sampling chamber. In one embodiment, the processor is configured to analyze the detector readings to determine $CO_2$ concentration within the fluid stream.

In one embodiment, the signal light source and the reference light source are driven at different operating frequencies (e.g., 50 kHz and 77 kHz), and the two corresponding signal components are separated from the detector readings by the processor using a Fourier transform or other suitable method. This allows the use of a single detector for both the signal light source and the reference light source.

In one embodiment, the light sources may produce light output in the mid-infrared (MIR) range. The combined light source may, for example, include a first light source centered at 4.2 µm and a second light source centered at 3.8 µm. The light sources may be light-emitting diodes. The system may also include separate filters for filtering the output of the two light sources to the desired spectral ranges, as well as a beam combiner for combining the filtered light from the two light sources into a single beam of light.

In one embodiment, the EGR probe may include a sampling chamber having two flow cells. The flow cells may be arranged in series and, if desired, may be separated by the lens. In this embodiment, the EGR probe may include a window that is disposed between the end of the pitch optical cable and the first flow cell. The window may be a collimator or other type of lens, if desired. The number of flow cells may vary from application to application.

In one embodiment, the EGR probe may include a mirror. The mirror may be disposed adjacent to the interior end of the probe to reflect the light beam from the pitch optical cable to the catch optical cable. The mirror may receive the light beam after it has passed from the pitch optical cable through the two flow cells and may reflect that light beam back through the two flow cells to the catch optical cable. As a result, the light beam may pass through each flow cell twice, thereby enhancing the absorption.

In one embodiment, the EGR probe is a single-port probe that is capable of being mounted in a single opening. The pitch optical cable and catch optical cable may be disposed adjacent to one another within a shared housing. The pitch cable may deliver light to the probe through a first end where it passes through the window, the first flow cell, the lens and the second flow cell to the second end. The mirror may be positioned at the second end and may reflect the light beam back toward the first end causing it to pass back through the second flow cell, the lens, the first flow cell, the window and into the catch optical cable. The catch optical cable may convey the reflected light beam back out of the first end of the probe to deliver it to the detector.

The processor may be connected to the output of the detector. The processor may be configured to separate the detector readings (or measurements) into a signal component and a reference component. The detector readings may be separated using a Fourier transform or other suitable method. The processor may also be configured to normalize the signal component as a function of the reference component using conventional normalization methods. Additionally, the processor may be configured to determine $CO_2$ concentration as a function of the normalized signal component.

In another aspect, the present invention provides a method for measuring spatial and temporal EGR fluctuations using an optical probe. The method generally includes the steps of: (a) providing an EGR probe in which portions of the pitch and catch optical path are includes in a single housing suitable for mounting within a single port, (b) producing first and second light beams with light over different spectra, (c) combining the first and second light beams into a combined light beam, (d) directing the combined light beam in a first direction through the housing via a pitch cable, (e) passing the combined light beam from the pitch cable through a fluid stream, for example, through a portion of the intake or exhaust manifold, (f) reflecting the combined light toward a catch cable, (g) directing the reflected beam through the housing in a direction opposite to the first direction via a catch cable, (h) receiving the light beam at a detector, and (i) determining the concentration of a component within the intake or exhaust manifold as function of the detected light beam. The step of determining the concentration of the component may include separating the detector output into signal and reference components, normalizing the signal component as a function of the reference component, and determining the concentration as a function of the normalized signal component.

In an alternative embodiment, the present invention provides a diagnostic system that utilizes a laser light source. A laser light source may provide a variety of benefits over an LED light source. For example, a laser provides linear sensitivity over a wide $CO_2$ range (e.g. $CO_2$ absorption is generally linear with respect to $CO_2$ concentration). A laser light source also has a narrow linewidth, which allows one to spectrally discriminate interfering species. It also allows simultaneous temperature and pressure measurements. For example, pressure may be determined based on broadening/narrowing of $CO_2$ line, and temperature may be determined based on the relative absorption of two $CO_2$ absorption transition with differing temperature dependencies of their absorption cross section. A laser light source may have more power and therefore may provide an improved signal-to-noise ratio, allow for faster measurements, and may enable multiple probes to be illuminated by a single light source. The use of multiple probes allows for measurements to simultaneously be taken at different locations to allow more extensive uniformity mapping and to accelerate validation and development.

In one embodiment, the laser light source is coupled to an EGR probe. In this embodiment, the laser may be a swept-wavelength, swept-λ, laser that repeatedly sweeps through a range of frequencies over time. In one embodiment, the sweep range is selected to include a distinctive $CO_2$ absorption region as well as zero absorption regions on opposite sides of the $CO_2$ absorption region. The sweep region may be selected to avoid regions that include significant water absorption. In one embodiment, the light source is a 2.7 μm laser having a sweep region centered at about 2.7082 μm. The sweep region may be from about 2.708 μm to about 2.7085 μm.

In one embodiment, the system is configured to measure and analyze $CO_2$ concentration in the intake manifold of an engine. In this embodiment, the system may implement a method of repeatedly sweeping the laser over the absorption features and, for each sweep, (i) collecting data from the detector, (ii) fitting the baseline to the measured data, (iii) calculating the transmitted and incident signal from the measured and baseline-fit profiles and a separate blank (background signal with the laser blocked or off) measurement, (iv) calculating the spectral absorbance from the calculated incident and transmitted signal profiles and fitting a lineshape to the measured data, (v) determining the $CO_2$ concentration, pressure and temperature from the lineshape, and (vi) repeat the process to allow time-resolved $CO_2$ concentration measurements.

In one embodiment, the laser light source is coupled to a plurality of EGR probes to facilitate simultaneous measurement and analysis at different locations from a single light source. In one embodiment, the output of the laser is split into a plurality of beams and each beam is routed to a separate EGR probe by corresponding pitch optics. The laser may be a swept wavelength laser and the output may be distributed to different probes by a beam splitter.

In one embodiment, the system includes a plurality of detectors and the light returning from each EGR probe is delivered to a separate light detector dedicated to that probe. Alternatively, the light returning from the EGR probes may be delivered to a single light detector and the processor may be capable of discriminating between the light returning from the different EGR probes. In a single detector embodiment, the system includes a beam combiner for combining the light returning from the plurality of EGR probes into a single light beam for detection purposes.

In one embodiment, the light beam associated with each probe is provided with a unique signature before the separate light beams are combined to allow the processor receiving the detector output to separate the light beams for analysis. The signature may be added before or after the light beam is passed through the probe. In one embodiment, each light beam is amplitude modulated at a different frequency, and the processor is configured to separate the detector readings (or measurements) into the different light beams using a Fourier transform or other suitable method.

In one embodiment, each light beam is amplitude modulated by attenuating the light beam at a frequency unique to that light beam. For example, the system may include a separate light chopper for each light beam. Each light chopper may be configured to introduce a unique modulation into the light beam, such as by effectively turning the light beam on and off at that light beam's unique modulation frequency.

The present invention provides a relatively simple diagnostic probe that is broadly applicable and suitable for use in applications with relatively severe packaging limitations. The EGR probe provides for the rapid processing of samples. As a result, the probe is capable of expanding development barriers. The use of a combined light source allows both signal and reference light beams to communicated through the probe using a single set of pitch and catch optics. Further, the combined light source allows the use of a single detector. The use of MIR LEDs provides a simple and cost effective combined light source that has appropriate absorption features for $CO_2$. The use of hollow wave guides provides a mechanism for conveying MIR light without unacceptable losses. The present invention may provide a diagnostic system that is capable of producing the data necessary to achieve efficiency, durability and emissions targets for advanced engine systems, particularly those using high EGR.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 9 is a perspective view of an engine intake manifold having apertures to receive the EGR probe.

FIG. 10 is a perspective view of the EGR probe within the intake manifold.

FIG. 11 is a schematic representation of the EGR probe within the intake manifold illustrating the adjustability of the depth of the probe.

FIG. 12 is a schematic representation of an alternative embodiment of the EGR probe.

DESCRIPTION OF THE CURRENT EMBODIMENT

Overview

Figure 1:
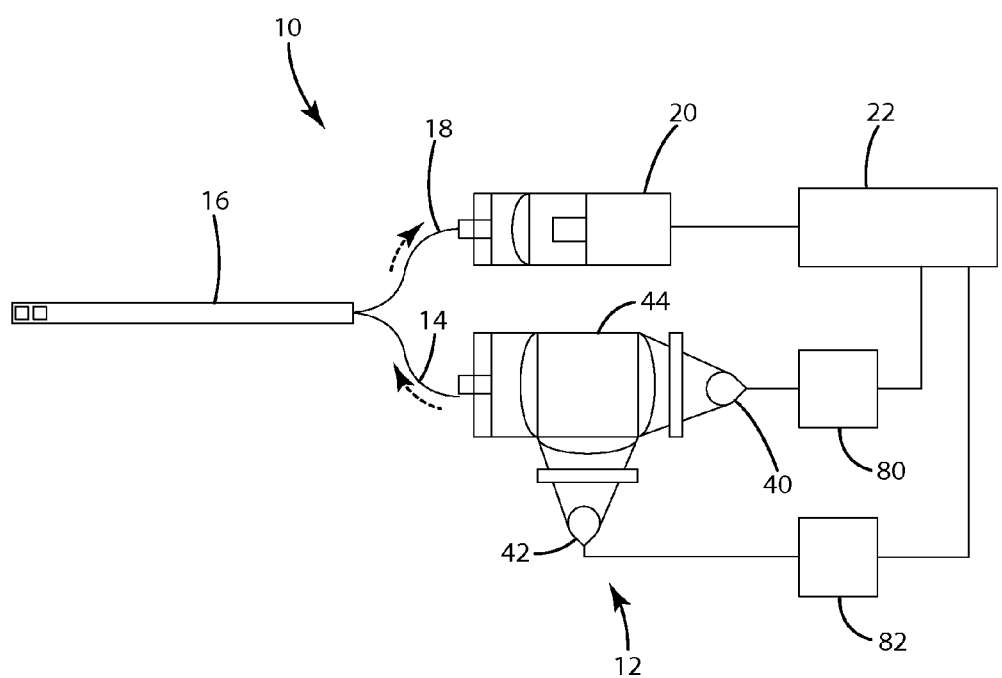
FIG. 1 is a schematic representation of a diagnostic system in accordance with an embodiment of the present invention.

A diagnostic system in accordance with an embodiment of the present invention is shown in FIG. 1 and generally designated 10. The diagnostic system 10 of this embodiment permits accurate measurement of $CO_2$ concentrations, and potentially other substances, within a fluid stream using absorption spectroscopy. The diagnostic system 10 generally includes a light source 12, a pitch optical cable 14, an EGR probe 16, a catch optical cable 18, a detector 20 and a processor 22 for determining $CO_2$ concentration based on the output of the detector 20. The light source 12 may be a mid-infrared (MIR) light source having a signal source 40 and a reference source 42 that are combined into a single light beam. In use, the reference source 42 is used to normalize the measurements from the signal source 40. The EGR probe 16 of this embodiment is a single-port probe capable of being installed in a single opening, such as in an aperture in an intake manifold I or an exhaust manifold (not shown).

The diagnostic system 10 may be used to measure $CO_2$ concentrations in essentially any application. In the illustrated embodiment, the diagnostic system 10 is used to measure $CO_2$ concentrations within an engine intake manifold I to determine the spatial and temporal non-uniformities of $CO_2$ in the fluid stream. For example, the system 10 may be used to measure cylinder-to-cylinder and cycle-to-cycle EGR fluctuations. In the context of engines with exhaust gas redistribution (EGR), the diagnostic system 10 may be used to quantify intake EGR fluctuations using $CO_2$ measurements.

For purposes of disclosure, the present invention is described in connection with a diagnostic system 10 used with an intake manifold I for an internal combustion engine (not shown) having an exhaust gas recirculation (EGR) system (not shown). In this context, the present invention can be used to assess spatial and temporal fluctuations in exhaust gas based on measurement of $CO_2$ concentration. The data collected by the diagnostic system 10 may be used to refine the EGR system, the intake manifold I, engine control parameters or other characteristics to improve performance of the engine and minimize $NO_X$ production. Although disclosed in the context of an EGR diagnostic system, the present invention may be readily adapted for use in other types of diagnostics. For example, the system 10 may allow diagnostics relating to other engine characteristics that can be assessed using $CO_2$ concentration. The diagnostic system 10 may also be used for applications that do not involve engines. The system may be modified to measure substances other than $CO_2$. For example, the light source, detector and processor may be modified to measure other substances, and provide diagnostics based on those substances can be performed.

Construction.

As summarized above, the present invention is described in connection with the measurement of $CO_2$ concentrations within an engine intake manifold I. For purposes of disclosure, the present invention is described in connection with a GM 1.9 L, 4-cylinder, direct injection diesel engine with Bosch common rail fuel injection, variable geometry turbo, electronic EGR valve, an intake swirl actuator, and a full-pass Driven control system. FIG. 9 shows an engine intake manifold I with four circular mounting ports (or apertures A)—one associated with each cylinder. The size, shape, configuration, number and location of apertures A may vary from application to application as desired. FIG. 10 shows the EGR probe mounted in the intake manifold I. As can be seen, the inner end of the EGR probe 16 may be positioned so that the flow cells 28 and 32 (described below) are located at the location where samples are to be taken. The intake manifold apertures A are capable of receiving an EGR probe 16 manufactured in accordance with an embodiment of the present invention. In this embodiment, the probe 16 is mounted to the intake manifold I via a standard bore-through SwageLok tube union boss, and positioned via a nonswaging ferrule. The EGR probe 16 may be mounted using other hardware, if desired. Although shown in an intake manifold, the EGR probe 16 may be installed in essentially any other structure containing a fluid stream, such as an exhaust manifold (not shown) or exhaust line (not shown).

Figure 3:
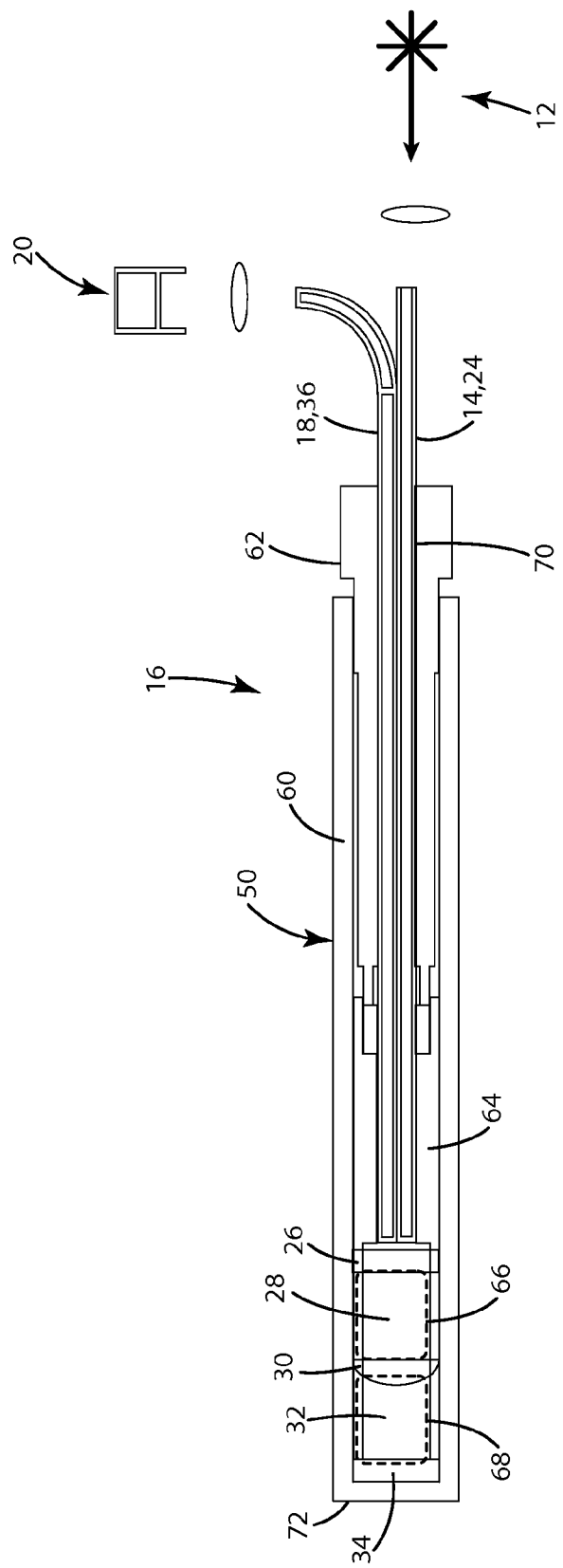
FIG. 3 is a schematic representation of the EGR probe, a light source and a detector.
Figure 4:
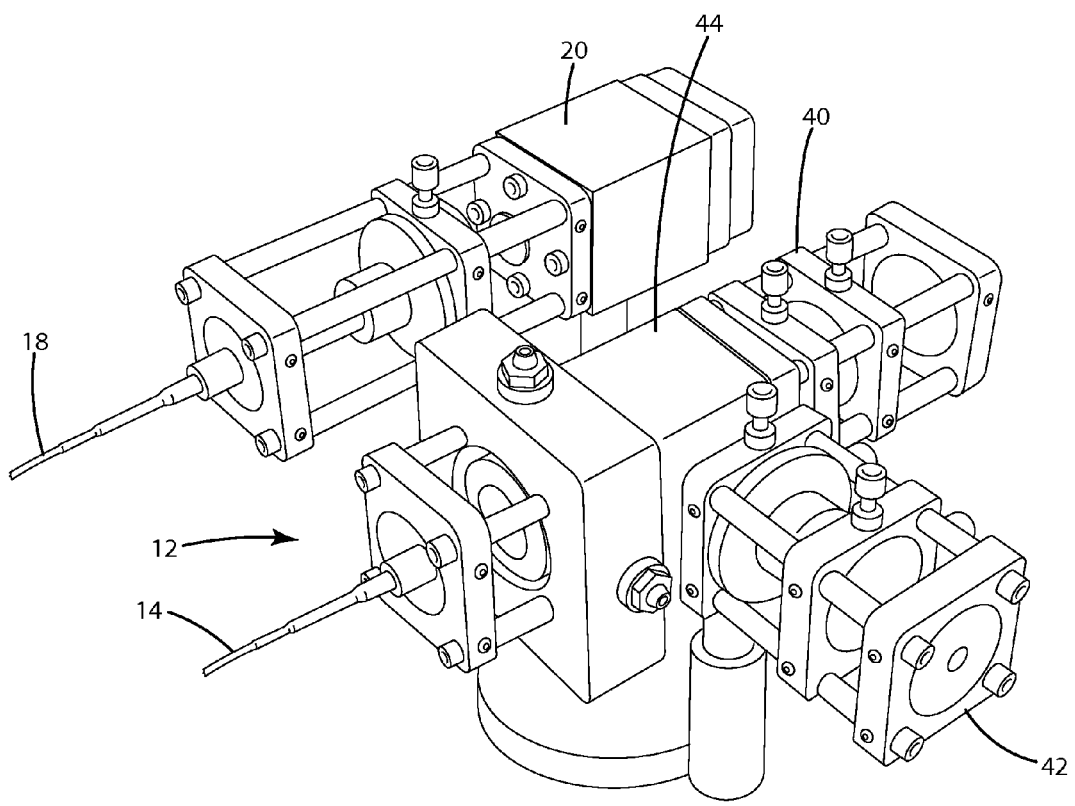
FIG. 4 is a perspective view of a combined light source and a detector.
Figure 5:
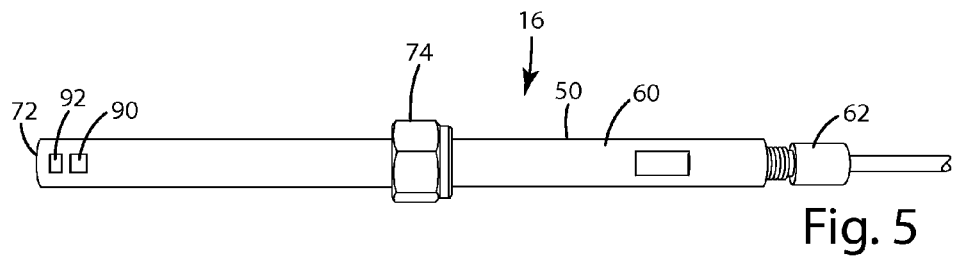
FIG. 5 is a side view of the EGR probe.
Figure 6:
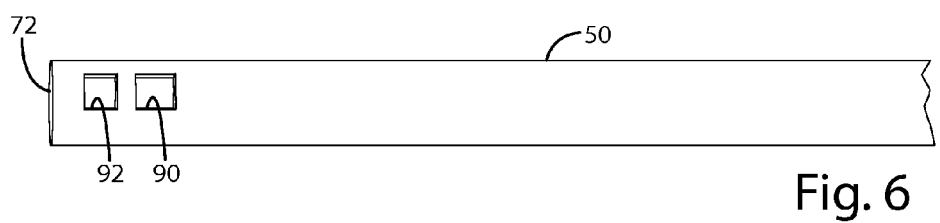
FIG. 6 is an enlarged side view of a portion of the EGR probe.
Figure 7:
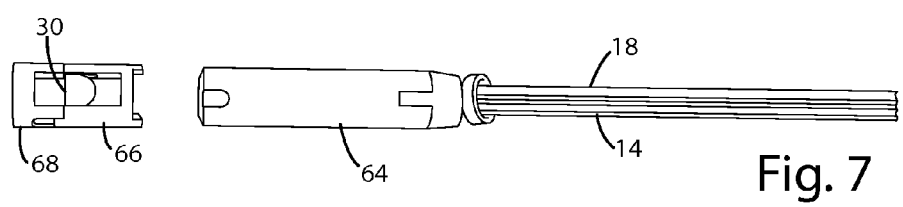
FIG. 7 is an enlarged side view of select subcomponents of the EGR probe.
Figure 8:
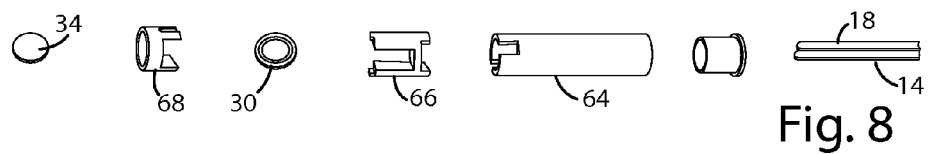
FIG. 8 is an exploded side view of select subcomponents of the EGR probe.

As noted above, FIG. 1 is a schematic representation of diagnostic system 10. As shown, the diagnostic system 10 of FIG. 1 generally includes a light source 12, a pitch optical cable 14, an EGR probe 16 with an internal sampling chamber 17, a catch optical cable 18, a detector 20 and a processor 22 for determining $CO_2$ concentration based on the output of the detector 20. The EGR probe 16 of the illustrated embodiment is a single-port probe capable of being installed in a single opening, such as aperture A in intake manifold I (See FIGS. 9-11). The EGR probe 16 of this embodiment includes a tubular housing 50 having a circular cross-section that corresponds with the shape of the aperture A in the intake manifold I. The housing 50 defines an internal void configured to define the sampling chamber 17 and to house the probe optics. In the illustrated embodiment, the sampling chamber 17 includes two separate flow cells (first flow cell 28 and second flow cell 32), and the probe optics are configured to direct the combined light beam through the flow cells. Referring now to FIG. 3, the probe optics of this embodiment include a pitch optical cable 24, a window 26, a lens 30, a mirror 34 and a catch optical cable 36. Pitch optical cable 14 and pitch optical cable 24 may be a single optical cable that extends from the light source 12 to the sampling chamber 17, or they may be separate optical cables that are joined together to form a continuous light path. Similarly, catch optical cable 18 and catch optical cable 36 may be a single optical cable that extends from the sampling chamber 17 to the detector 20, or they may be separate optical cables that are joined together to form a continuous light path. The housing 50 may include an outer tube 60, an inner tube 62, a mount 64, a first spacer 66 and a second spacer 68. In this embodiment, the outer tube 60 is approximately 3/8 of an inch in diameter and is configured to be fitted into a 3/8 of an inch diameter aperture A in the intake manifold I. The outer tube 60 is hollow and includes a closed inner end 72. As perhaps best shown in FIG. 6, the outer tube 60 defines sampling ports 90 and 92 that allow fluid from outside the EGR probe 16 to flow through the flow cells 28 and 32. The mirror 34, first spacer 66, lens 30, second spacer 68, window 26 and mount 64 are stacked within the hollow outer tube 60. The inner tube 62 may include an internal bore 70 configured to receive and support the pitch and catch optical cables. The inner tube 62 may be threadedly secured within the outer tube 60 to secure the various components of the EGR probe 16. A nut 74 may be fitted around the outer tube 60 for securing the EGR probe 16 is an aperture A. For example, the nut 74 may be a Swagelok nut. If desired, the EGR probe 16 may utilize a non-swaging ferrule to allow translation. The size, shape and configuration of EGR probe 16 is merely exemplary, and the EGR probe may vary from application to application. For example, the size, cross-sectional shape and internal configuration of the housing 50 may vary depending on the application. Similarly, the optical components may also vary depending on the application.

An alternative EGR probe 16' is shown in FIG. 12. In this embodiment, the EGR probe 16' is generally identical to EGR probe 16, except as described. As shown, EGR probe 16' includes essentially the same optics as EGR prober 16 having pitch and catch optical cables 24' and 36', window 26', first flow cell 28', lens 30', second flow cell 32' and mirror 34'. However, in this embodiment, the housing 50' is somewhat different having a main tube 60' and an end tube 62' that are joined end to end and cooperatively form an internal void to contain the probe optics and supporting structures. The main tube 60' and end tube 62' may be welded together or other joined as desired. The housing 50' includes a mount 64' that is fitted into the main tube 60' and the end tube 62'. The mount 64' may be threaded or otherwise secure to main tube 60' and/or the end tube 62'. The housing 50' also includes a spacer 66' that is fitted into the end tube 62' where it is disposed between the mirror 34' and the lens 30'.

Figure 2A:
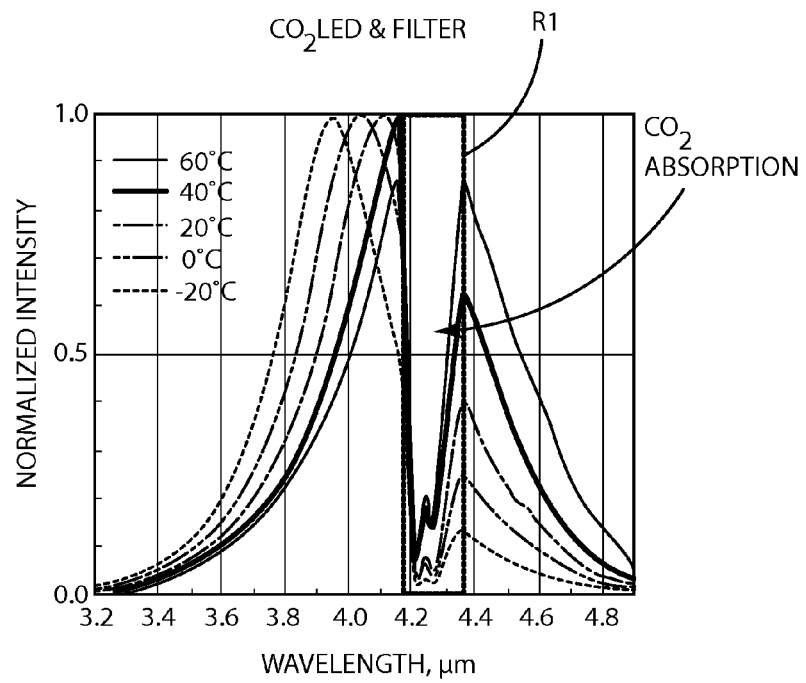
FIG. 2A is an emission spectra profile for a signal light source with a highlighted region showing the region where $CO_2$ absorbs light.
Figure 2B:
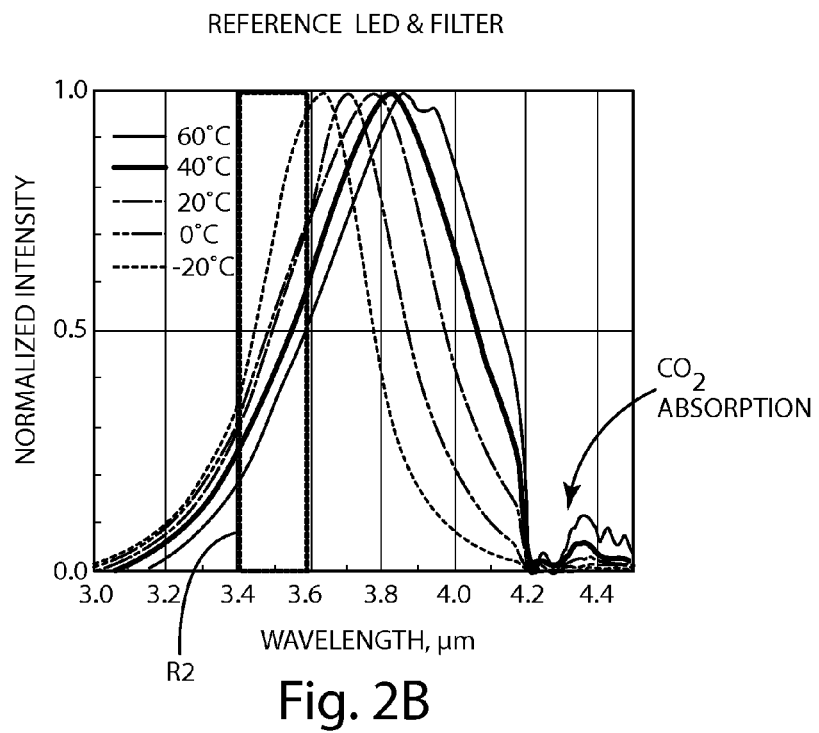
FIG. 2B is an emission spectra profile for a reference light source with a highlighted region showing a region where $CO_2$ does not absorb light effectively.

In the illustrated embodiment, the EGR probe 16 is intended for use with a light source 12 that produces light in the mid-infrared (MIR) range. This spectral range includes $CO_2$ absorption features that are sufficient to allow accurate measurement of $CO_2$ concentration. With a MIR light source, the pitch optical cable 24 and the catch optical cable 36 may be hollow waveguides configured for use in conveying MIR light. Hollow waveguides may provide improved light transmission as compared to other types of optical fibers or light guides. In the illustrated embodiment, the light source 12 is a combined light source that includes light produced by a signal source 40 and a reference source 42. In this embodiment, the EGR probe 16 is intended for use in measuring $CO_2$ concentration. As a result, the signal source 40 may be an MIR LED that produces light over a spectral range that is centered at 4.2 µm and overlaps the $CO_2$ absorption features near 4.3 µm. The characteristics of the signal source 40 may vary, for example, depending on the substance to be detected. The reference source 42 may be an MIR LED that produces light over a spectral range that is centered at 3.8 μm and does not coincide with $CO_2$ absorption features or other known interference species. The output of each light source 40, 42 may be spectrally filtered as shown in FIGS. 2A and 2B to provide the desired light beam. FIG. 2A shows the spectral range R1 of the filtered signal light source. FIG. 2B shows the spectral range R2 of the filtered reference light source. With this configuration, the reference source 42 may be used by the processor 22 to normalize the measurements of the signal source 40 taken by the detector 20.

The spectrally-filtered output of the signal source 40 and the spectrally-filtered output of the reference source 42 are combined, for example, using a beam combiner 44. The beam combiner 44 may be essentially any beam combiner or beam combiner/splitter capable of combining the light produced by the signal source 40 and the light produced by the reference source 42 into a composite light beam. The combined light beam is conveyed to the EGR probe 16 by pitch optical cable 14 and pitch optical cable 24. The light is output from the pitch optical cable 24 through window 26 into first flow cell 28. After passing through first flow cell 28, the light passes through lens 30 and second flow cell 32. The light then reflects off of mirror 34 and passes back through second flow cell 32, lens 30, first flow cell 28 and window 26. The mirror 34, lens 30 and window 26 are configured so that the returning light is directed into catch optical cable 36. Catch optical cable 36 conveys the light to catch optical cable 18. Catch optical cable 18 conveys the light to detector 20.

In this embodiment, the signal and reference light sources are driven at different modulation frequencies, such as 50 kHz and 77 kHz. These particular modulation frequencies are merely exemplary and the modulation frequencies may vary from application to application. In practice, it is desirable for the modulation frequencies to be sufficiently distant from one another so that the signals can be adequately separated by the processor 22. In the illustrated embodiment, the signal light source 40 is operated by a signal driver 80 that modulates the signal light source 40 at 50 kHz, and the reference light source 42 is operated by a reference driver 82 that modulates the reference light source at 77 kHz. The drivers 80 and 82 may be enabled by the processor 22, as shown in FIG. 1. This configuration is merely exemplary and the light sources may be driven using other electronic controls. For example, the processor 22 may be capable of directly driving the two light sources, 40 and 42, at the desired modulation frequencies.

The detector 20 may be essentially any photodetector capable of producing signals representative of the light beam returned from the EGR probe 16. The output of the detector 20 is connected to processor 22. The processor 22 may be essentially any processor capable of analyzing the detector output to provide $CO_2$ measurements. As noted above, the light beam passed through the EGR probe 16 is a combined light beam that is a composite of the light produced by the signal source 40 and the reference source 42. The processor 22 is configured to separate the combined light beam into a signal component and a reference component. In this embodiment, the signal component and reference component are resolved from the detector output using a Fourier transform. The processor 22 is also configured to normalize the signal component using the reference component. Given that the reference source is selected to include a spectral range that does not include any significant $CO_2$ absorption features, the reference component can be used to provide a base line for normalizing the signal component. The processor 22 is also configured to determine the $CO_2$ concentration in the fluid stream from the normalize signal component. The $CO_2$ concentration may be determined using conventional absorption spectroscopy methodologies.

Method of Use.

As noted above, the diagnostic system 10 is described in the context of an engine diagnostic tool. In this application, the diagnostic system 10 may be used to measure $CO_2$ concentrations within an engine intake manifold to determine spatial and temporal nonuniformities of $CO_2$ in the fluid stream. For example, the system 10 may be used to measure cylinder-to-cylinder and cycle-to-cycle $CO_2$ fluctuations. In the context of engines with exhaust gas redistribution (EGR), the $CO_2$ measurements taken by the diagnostic system 10 may be used to quantify intake EGR fluctuations. The data collected by the diagnostic system 10 may be used simply to characterize performance, or it may be used to refine the EGR system, the intake manifold I, engine control parameters or other characteristics to improve performance of the engine and minimize $NO_X$ production.

In the illustrated embodiment, the diagnostic system 10 is used to measure $CO_2$ concentrations within an engine intake manifold I. The engine intake manifold I includes a plurality of apertures A that allow the EGR probe 16 to be selectively installed in the intake manifold I at different locations. In the illustrated embodiment, the intake manifold I has four apertures A—one associated with each cylinder. As noted above, the EGR probe may be secured within an aperture A using a conventional Swagelok union. Sealant may be used to reduce the potential for leaking around the union. The number and location of the apertures may vary from application to application. In this application, the EGR probe 16 may be used to assess spatial and temporal fluctuations in $CO_2$ concentrations. For example, the EGR probe 16 may measure the $CO_2$ concentrations at various locations within the intake manifold to determine the spatial uniformity of exhaust gas recirculation. For this purpose, the present invention may use a single EGR probe 16 that may be moved from time to time to measure $CO_2$ concentrations at different locations. In one embodiment, the EGR probe 16 may be used to measure the $CO_2$ concentrations at each cylinder to assess the cylinder-to-cylinder uniformity of recirculated exhaust gas. As an alternative to a single probe 16, the system 10 may include a plurality of EGR probes 16 that allow simultaneous measurements from different locations within the manifold. In some application, a separate diagnostic system may be used for each location, and the output of the different systems may be compared to assess the differences.

As an alternative to measuring spatial uniformity, the EGR probe 16 may measure the $CO_2$ concentrations at a given location over time to determine changes in $CO_2$ concentration over time. In this application, the temporal differences may be determined to assess cycle-to-cycle uniformity of the EGR system. A single EGR probe 16 may be used to measure $CO_2$ concentrations at a single location over time, or a plurality of EGR probes may be used to simultaneously measure $CO_2$ concentrations at different locations. As an alternative to cycle-to-cycle measurements, the present invention may be used to take measurements at essentially any timescale (e.g. individual valve events, or intra-valve events, or longer term drift or variations). The diagnostic system 10 may be used to perform other types of diagnostics that depend on $CO_2$ concentration or the concentration of other substances that may be measured using the present invention.

In one application, the method generally includes the steps of: (a) providing an EGR probe 16 in which the pitch and catch optical path are includes in a single housing suitable for mounting within a single port, (b) producing a signal light beam and a reference light beam over different spectra, (c) combining the signal and reference light beams into a combined light beam, (d) directing the combined light beam in a first direction through the housing via a pitch cable, (e) passing the combined light beam from the pitch cable through the fluid stream to be measured (e.g. a portion of the intake or exhaust manifold), (f) reflecting the combined light toward a catch cable, (g) directing the reflected beam through the housing in a direction opposite to the first direction via a catch cable, (h) receiving the light beam at a detector, and (i) determining the concentration of a component within the intake or exhaust manifold as function of the detected light beam.

In this embodiment, the signal light source and reference light source are modulated at different frequencies (e.g., 50 kHz and 77 kHz, respectively) so that they can be separated from the detector signals. For example, the signal and reference components of the combined light beam can be separated by processor 22 using a Fourier transform. In this embodiment, the signal light source and reference light source may be modulated using separate drivers, such as signal driver 80 and reference driver 82.

In the illustrated embodiment, the signal and reference light beams are combined into a single light beam using a beam combiner/splitter. The beam combiner may be essentially any beam combiner or beam splitter capable of combining the MIR output of the signal and reference light sources into a single composite light beam.

When measuring spatial fluctuations with a single probe, the method may also include the steps of (a) installing the EGR probe 16 in a first location in the intake manifold I, (b) taking $CO_2$ measurements at the first location, (c) installing the EGR probe 16 in a second location, (d) taking $CO_2$ measurements at the second location and (e) repeating these steps for each additional location to be measured. The location may be varied by moving the EGR probe 16 from one aperture A to another and/or by varying the depth of EGR probe 16 within an aperture A. FIG. 11 is a schematic representation of the EGR probe 16 in the intake manifold I. The depth of the EGR probe 16 within the intake manifold I can be adjusted to essentially any location along line L.

When measuring spatial fluctuations with a plurality of probes, the method may also include the steps of (a) installing a separate EGR probe 16 in each desired location within the intake manifold I and (b) simultaneously taking $CO_2$ measurements at each location using the separate EGR probes 16.

When measuring temporal fluctuations, the EGR probe 16 or EGR probes 16 may be installed in the desired location(s) in the engine intake manifold I and a plurality of measurements may be taken over time. The number of measurements and the timing between measurements vary from application to application, as desired.

The measurements produced by the detector 20 are processed by processor 22 to determine the concentration of $CO_2$. This process may include the steps of: (a) separating the detector measurements into a signal component and a reference component; (b) normalizing the signal component using the reference component and (c) determining the $CO_2$ concentration from the normalized signal component. The step of separating the detector measurements into a signal component and a reference component may include processing the measurements using a Fourier transform that separates the components based on their different modulation frequencies. Such processing also minimizes the effect of detector noise on the measurement precision. The step of normalizing the signal component may include adjusting the signal component as a function of the reference component. Once the signal component has been normalized, the $CO_2$ concentration may be determined using conventional absorption spectroscopy methodologies, which will not be described in detail here.

Laser-Based Embodiments.

Figure 13A:
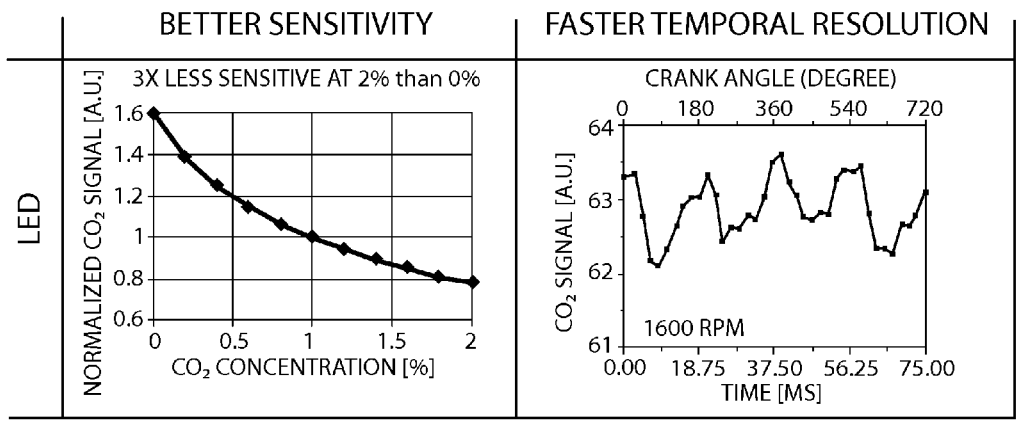
FIG. 13A-B are plots showing the sensitivity of LED and laser light sources.
Figure 13B:
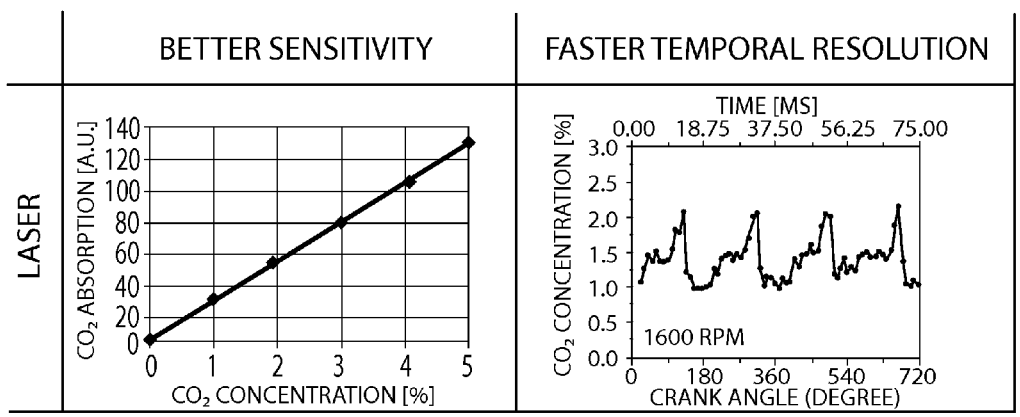

A diagnostic system in accordance with an alternative embodiment of the present invention may include a laser light source. A laser light source may provide a variety of benefits over other light sources. For example, unlike typical MIR LEDs, a laser provides substantially linear sensitivity over a wide range of $CO_2$ concentrations. This can be seen by comparing the graphs shows in FIGS. 13A and 13B. FIG. 13A shows that sensitivity of a 4.3 μm-MIR-LED-based system, which drops significantly over increased $CO_2$ concentrations. On the other hand, FIG. 13B shows that $CO_2$ absorption is essentially linear with increased $CO_2$ concentration with a 2,7-μm-laser-based system. Further, a laser light source has a narrow line width (or bandwidth), which, among other things, allows spectral discrimination of interfering species. A laser light source also allows simultaneous temperature and pressure measurements. For example, pressure may be determined based on broadening/narrowing of $CO_2$ line, and temperature may be determined based on the relative absorption of two $CO_2$ absorption transition with differing temperature dependencies of their absorption cross section. Other meaningful benefit results from the higher output power provided by a laser. As a result of its higher power, a laser light source may provide an improved signal-to-noise ratio, thereby improving the accuracy of measurements. The higher power may also allow for faster measurements, thereby providing the potential to increase the speed at which diagnostics can be performed. Further, a laser may have sufficient power to allow multiple probes to be illuminated by a single light source. The use of multiple probes allows for measurements to simultaneously be taken at different locations. This may allow more extensive uniformity mapping and accelerate validation and development.

Figure 14:
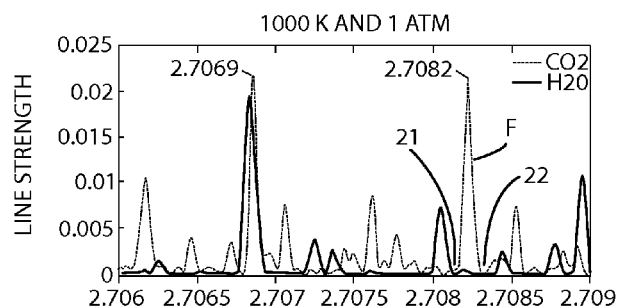
FIG. 14 is a graph of line strength to wavelength over a range of frequencies.

The laser may be essentially any type of laser capable of providing sufficient output over the desired frequency range. In the illustrated embodiments, the laser is a swept-wavelength, swept-λ, laser capable of producing light output over a defined sweep range. In operation, the laser may continuously and repeatedly sweep through a desired frequency range. The sweep range may vary from application to application. In the illustrated embodiment, the laser is configured for use with a diagnostic system intended to measure $CO_2$ concentration in the intake manifold of an engine. In this context, the sweep range of the laser is selected to include a distinctive $CO_2$ absorption region that has suitable line strength. Further, to assist in normalizing the measurements to a baseline, the sweep range is also selected to include zero absorption regions on opposite sides of the $CO_2$ absorption region. The term "zero absorption region" is used herein to refer to a region with sufficiently low absorption that it can be used in determining a baseline for normalizing measurements, and is not limited to regions in which there is absolutely no absorption. The sweep range may also be selected to avoid regions that include significant water absorption or absorption from other source of interference. FIG. 14 shows a graph of line strength to wavelength for a range of 2.706 μm to 2.709 μm. From this graph it can be seen that there is a $CO_2$ absorption feature F with high line strength centered at about 2.7082 μm. This area of the graph also shows zero absorption regions Z1 and Z2 on opposite sides of the $CO_2$ absorption feature. As can be seen, the zero absorption regions are essentially free of absorption by $CO_2$ water. In view of the data provided in FIG. 14, the diagnostic system may include a 2.7

μm laser light source having a sweep range centered at about 2.7082 μm. To include the zero absorption regions, the sweep range may be from about 2.708 μm to about 2.7085 μm. This sweep range is exemplary and the light source may implement other sweep ranges from application to application.

Figure 15:
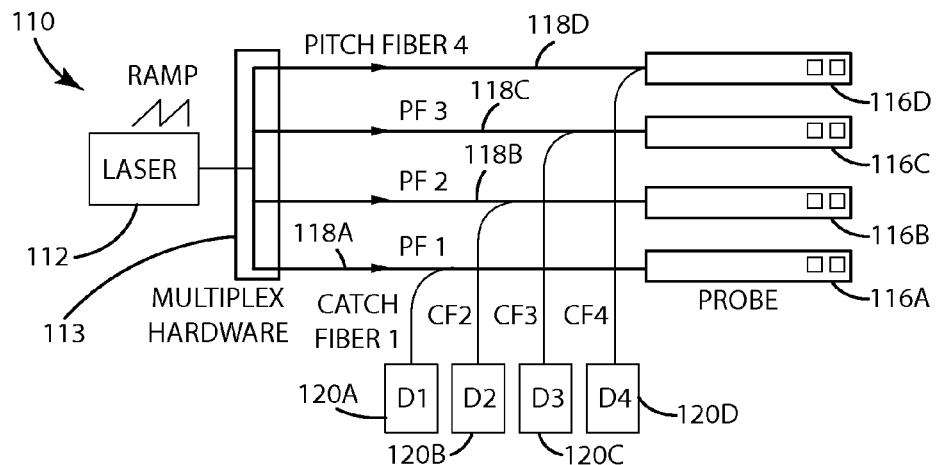
FIG. 15 is a schematic representation of a four-probe laser-based system using separate detectors for each probe.
Figure 17:
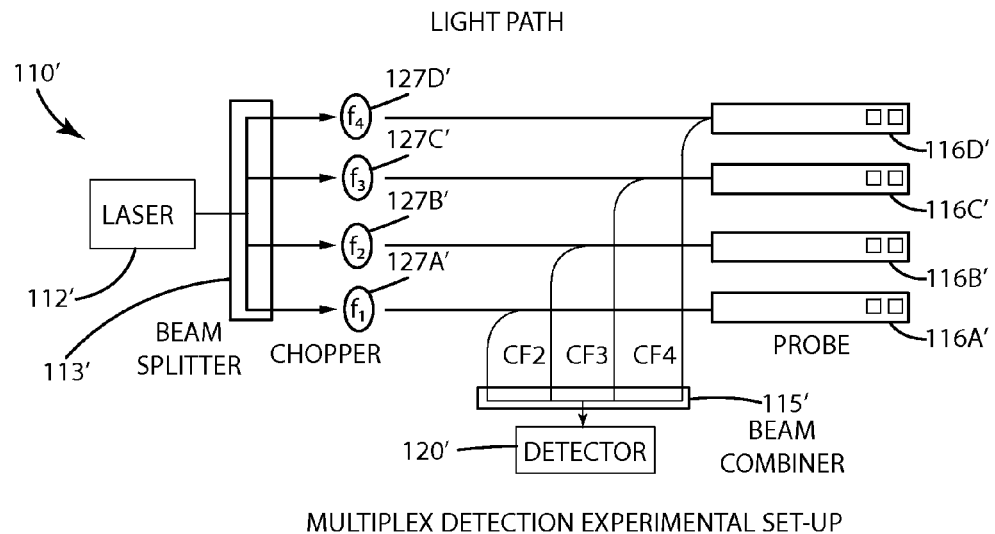
FIG. 17 is a schematic representation of a four-probe laser-based system using a single detector.
Figure 19A:
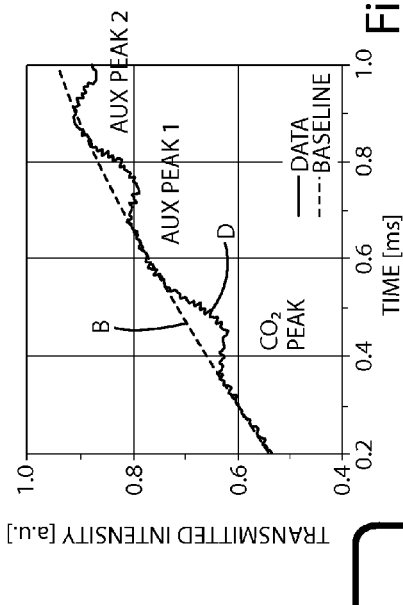
FIGS. 19A-D are plots illustrating the general steps of a method for measuring and analyzing $CO_2$ concentration in an engine.
Figure 19B:
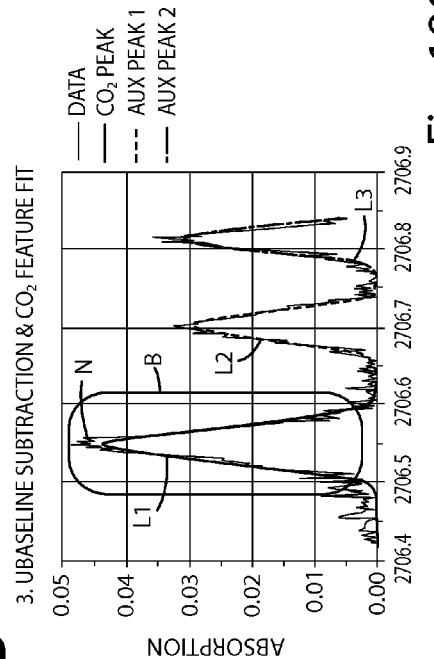

As noted above, the laser may function as a light source for a single probe or for a plurality of probes. For example, with reference to FIG. 3, light source 12 may be a laser providing light to probe 16. FIGS. 15 and 17 show alternative embodiments in which a laser functions as a light source for a plurality of probes. Regardless of the number of probes, the laser-based diagnostic system may be used in connection with a variety of different measurement and analysis methods. For purposes of disclosure, operation of a single probe laser-based diagnostic system will now be described in connection with one method of operation. In this embodiment, the system is configured to measure and determine $CO_2$ concentration in the intake manifold of an engine over time. In this embodiment, the system implements a method of repeatedly sweeping the laser over the absorption features. More specifically, the laser repeatedly and continuously sweeps through the sweep range. As noted above, in this application, the sweep range may be from about 2.708 μm to about 2.7085 μm. The method of this embodiment generally includes the steps of, for each pass through the sweep range, (i) collecting data from the detector, (ii) fitting the baseline to the measured data, (iii) calculating the transmitted and incident signal from the measured and baseline-fit profiles and a separate blank (background signal with the laser blocked or off) measurement, (iv) calculating the spectral absorbance from the calculated incident and transmitted signal profiles and fitting a lineshape to the measured data, (v) determining the $CO_2$ concentration, pressure and temperature from the lineshape, and (vi) repeating the process to allow time-resolved $CO_2$ concentration measurements. This process may be implemented using the Beer-Lambert Law, which is shown in FIG. 20. One implementation of this general process will now be described in more detail with reference to FIGS. 19A-D. FIG. 19A shows the detector measurements over time for four sequential spectral sweeps of the laser. As can be seen in the data, the laser undergoes a generally linear increase in intensity from one end of each sweep range to the other end of that sweep range. This general spectral increase in laser power is a practical result of the nature of the laser and must be characterized in order to determine the spectrally varying incident irradiance, for example, as described below. In this process, the detector measurements associated with a single sweep are analyzed together to produce a single data point. For example, the measurements occurring during the timeframe associated with the first pass through the sweep range of the laser (temporal window A) are grouped together and processed to produce a single point in the plot of FIG. 19D. FIG. 19A shows the data from four sequential passes through the sweep range, thereby providing data for use in producing four sequential data points, namely data point 1 through data point 4 of FIG. 19D. It should also be noted that because the laser is changing wavelength to move through the sweep range over time, there is a correlation between time and laser output wavelength in the measured data.

For each collection of data associated with a single data point, the processor analyzes the data to fit (or determine) the baseline for the measured data. The data can be analyzed to determine the baseline using computational methods. A variety of computational methods are known to those skilled in the art. This is illustrated in FIG. 19B, which is a plot of transmitted spectral irradiance over time showing one line D representing the measured data and another line B representing the computationally determined baseline or spectrally varying incident irradiance through the laser sweep.

Figure 19C:
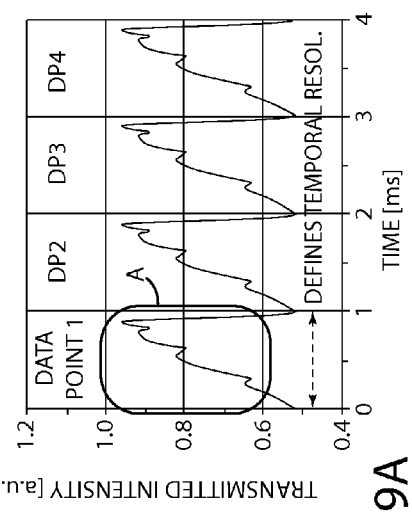
Figure 19D:
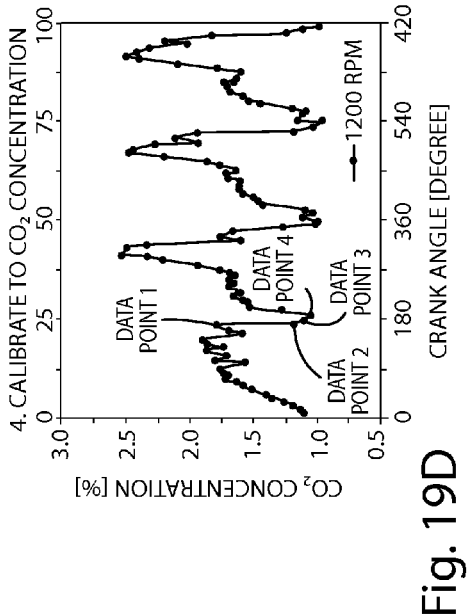
Figure 20:
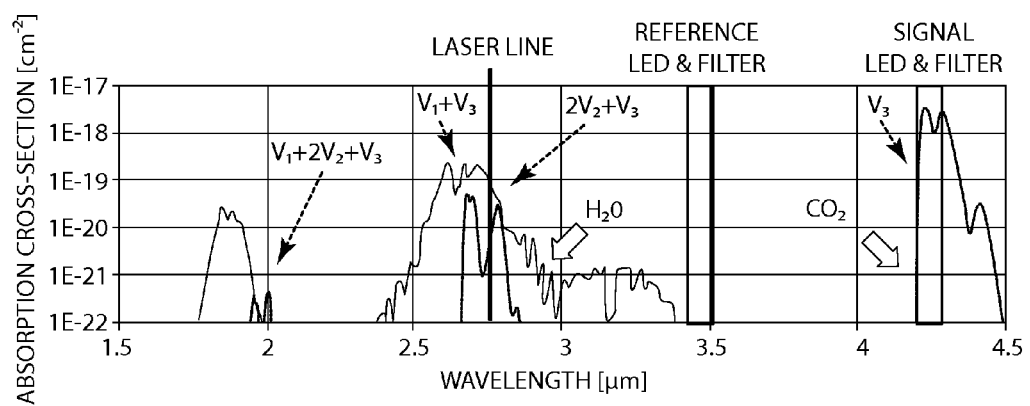
FIG. 20 is a representation of the Beer-lambert Law.

Once the baseline has been determined, it along with the measured spectral irradiance and a separate blank measurement may be used by the processor to determine the spectral absorbance (natural log of the transmitted to incident irradiance ratio) profile, as shown in FIG. 19C. The spectral absorbance profile is shown as line N in FIG. 19C. The processor may then produce one or more lineshapes that fit to the spectral absorbance profile. In this embodiment, the measured data included three peaks that correspond to a $CO_2$ feature and two auxiliary features. In this embodiment, the processor creates three lineshape—one corresponding to each of the peaks. The lineshapes are shown as line L1, L2 and L3 in FIG. 19C. The lineshapes may be produced using computational methods. A variety of such methods are known to those skilled in the art.

Once the measured data has been used to determine the spectral absorbance profile and the lineshape(s) have been fit, the $CO_2$ concentration can be determined based on the $CO_2$-feature lineshape, and a calibration that relates the spectrally integrated absorbance to the $CO_2$ concentration; via the Beer-Lambert Law. The $CO_2$ concentration can then be incorporated into the plot shown in FIG. 19D, which plots $CO_2$ concentration versus engine crank angle. This allows analysis of the $CO_2$ variations throughout a complete engine cycle (crank angle range of 0-720 degrees). In the illustrated embodiment, the data in area B of FIG. 19C is processed together to provide a single data point in FIG. 19D; the process is repeated upon the subsequent laser spectral sweep to determine the subsequent $CO_2$ point in FIG. 19D.

In addition to providing $CO_2$ concentration, the normalized data and/or the lineshapes may be analyzed to provide pressure and temperature readings. For example, with regard to pressure, the line width of the $CO_2$ feature shown in spectral window B of FIG. 19C may be analyzed in accordance with known methods to provide pressure. As another example, temperature can be determined based on the fit of the spectral absorbance in spectral window B in accordance with known methods; notably, this region contains a second $CO_2$ transition around 2706.5 nm that is weak at this temperature, and the two $CO_2$ transitions have differing temperature dependencies of their absorption cross sections.

Figure 16:
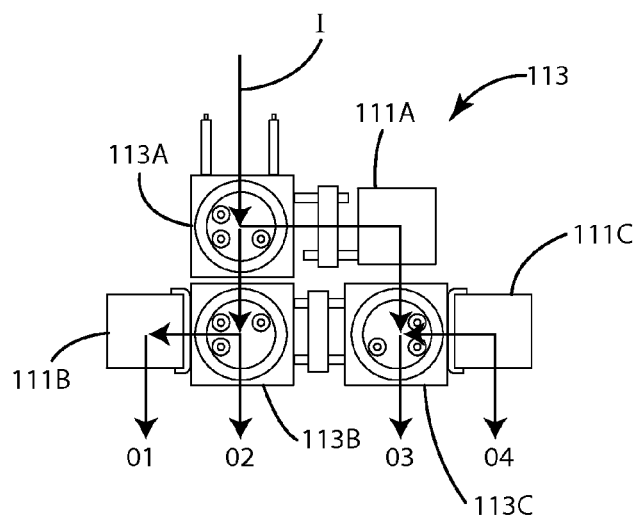
FIG. 16 is an illustration of a beam splitter configured to split the light from a laser light source into a plurality of separate light beams for distribution to separate probes.

As noted above, the use of a laser light source allows the diagnostic system to include a plurality of probes that receive light from a single light source. One implementation of a multiple-probe system is shown in FIG. 15. In this embodiment, the system 110 includes a laser configured to simultaneously provide light to plurality of probes 116a-d, The system 110 may include a beam splitter arrangement 113 that is configured to divide the output of the laser 112 into a plurality of separate, but generally identical, beams corresponding to the number of probes 116a-d (in this case, four). The beam splitter arrangement 113 may be essentially any component capable of splitting the beam into the desired number of beams, but in the illustrated embodiment is a mirror-and-beam-splitter-based system that divides the input beam into four output beams. A mirror-and-beam-splitter-based system arrangement 113 is shown in FIG. 16. As represented by the overlaid lines, a single light beam I enters the beam splitter arrangement 113 and passes through a series of mirrors 111a-c and beam splitters 113a-c to produce four output beams O1-O4. In this embodiment, the beam splitters 113a-c are 50:50 beam splitters and the light beam I is split into four essentially identical output beams O1-O4.

In this embodiment, the pitch and catch optics, such as the cables and other optical components arranged along the pitch and catch light paths may be selected for use with laser-generated light beams. For example, the pitch and catch optical fibers may be inert-gas-purged hollow waveguides.

In the embodiment of FIG. 15, the diagnostic system 110 includes a separate light detector 120a-d for each EGR probe 116a-d. In this embodiment each catch optical fiber 118a-d is routed from an EGR probe 116a-d to the corresponding detector 120a-d. A single processor or collection of processor may be couple to the detectors 120a-d to collect and analyze the measured data. For example, the measured data may be collected and analyzed in accordance with the method described above in connection with the single probe laser diagnostic system. In this embodiment, there are four probes simultaneously producing separate data streams. The data stream from each probe may be separately collected and measured using the methods discussed above in connection with the single probe laser diagnostic system.

In an alternative embodiment shown in FIG. 17, the diagnostic system 110' generally includes a single laser light source 112', a beam splitter 113', a plurality of EGR probes 116a-d', a beam combiner 115' and a single detector 120' that is capable of detecting light from all of the EGR probes 116a-d'. In this embodiment, the processor is configured to discriminate between the light returning from the different EGR probes 116a-d' so that the data from each probe 116a-d' can be separately analyzed. The beam combiner 115' may be essentially any component capable of combining the light returning from the plurality of EGR probes into a single light beam for detection by detector 120'. In the illustrated embodiment, the beam combiner 115' is a mirror-and-beam-splitter-based beam combiner that is arranged in essentially reverse of the beam splitter 113'.

To allow the processor to discriminate between the light returning from the different probes 116a-d', the light beam associated with each probe 116a-d' is provided with a unique signature. The signature may be added to each light beam before or after the light beam is passed through its corresponding probe 116a-d'. For example, the signature may be separately added to each light beam after the light beam is split and before it passes into the probe. As another example, the signature may be separately added to each light beam after they return from the probes 116a-d' and before they are combined. In the illustrated embodiment, the signature is added to each light beam by amplitude modulating the light beam at a unique frequency. In one embodiment, each light beam is amplitude modulated by attenuating the light beam at a frequency unique to that light beam. For example, the system may include a separate light chopper 127a-d' for each light beam. Each light chopper 127a-d' may be configured to introduce a unique modulation into the corresponding light beam. For example, the choppers 127a-d' may turn the light beam on and off (or otherwise attenuate the light beam) at that light beam's unique modulation frequency.

Figure 18:
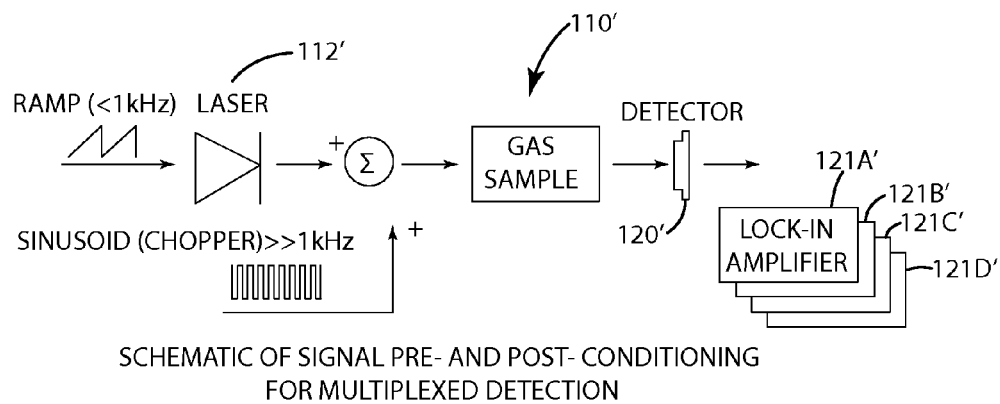
FIG. 18 is a schematic representation of the pre- and post-conditioning stage for multiplexed detection.

The processor is coupled to the output of the detector 120' and receives a signal representative of a composite of the light beams received from each of the four probes 116a-d'. The composite signal may be separated into its component parts for analysis using post-processing of the output signal from the detector 120' using a Fourier transform or other suitable method. As an alternative, the system 110' may include a plurality of lock-in amplifiers 121a-d' for separating the composite single into its component parts. For example, in the embodiment shown in FIG. 18, the system 110' may include four lock-in amplifiers 121a-d', each of which are uniquely associated with one of the four probes 116a-d'. Each lock-in amplifier 121a-d' is configured to isolate the component part of the composite signal corresponding to its associated probe 116a-d'.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. An apparatus for determining concentration of a substance in a fluid stream, the apparatus comprising:
    a laser light source coupled to a first end of a pitch optic cable, the laser light source being a swept-$\lambda$ laser configured to produce light output over a sweep range that includes a region having a significant absorption feature of the substance and at least one region of substantially zero absorption;
    a lens disposed proximate a second end of the pitch optic cable for directing the light through a sampling chamber to a mirror;
    a catch optic cable having a second end disposed proximate said lens;
    a catch optic affixed to a first end of said catch optic cable, said catch optic including a detector, said detector providing an output signal representative of light intensity across said sweep range; and
    a processor coupled to said detector, said processor configured to determine said concentration as a function of said output signal.

2. The apparatus of claim 1 wherein said processor is configured to normalize said output signal using a baseline established as a function of said zero absorption region and to determine said concentration as a function of said normalized signal.

3. The apparatus of claim 1 wherein said substance is $CO_2$ and said laser has a sweep range centered at about 2.7082 µm.

4. The apparatus of claim 3 wherein said laser has a sweep range including substantially zero absorption regions on opposite sides of said $CO_2$ absorption feature.

5. The apparatus of claim 4 wherein said laser has a sweep range from about 2.708 µm to about 2.7085 µm.

6. A diagnostic system for determining $CO_2$ concentration comprising:

a swept-λ laser having a sweep range including a $CO_2$ absorption feature and at least one substantially zero absorption region;

a beam splitter disposed adjacent to said laser to split an output light beam of said laser into a plurality of light beams;

a plurality of probes coupled to said beam splitter, each of said probes being uniquely associated with a corresponding one of said plurality of light beams, each probe including:

a single port housing;

a sampling chamber defined within said housing;

a pitch optical cable disposed within said housing, said pitch optical cable conveying said light beam to said sampling chamber;

a catch optical cable disposed within said housing, said catch optical cable conveying said light beam from said sampling chamber;

a mirror disposed adjacent said sampling chamber for reflecting said light beam to said catch optical cable; and a processor for determining $CO_2$ concentration as a function of at least one light beam conveyed from said sampling chamber of at least one of said plurality of probes.

7. The system of claim 6 further including a light combiner operatively coupled to each of said plurality of probes, said light combiner configured to combine the light beams from each of said plurality of probes into a single composite light beam; and a detector for producing an output signal representative of light intensity in said composite light beam.

8. The system of claim 7 further including a processor coupled to said detector, said processor configured to determine $CO_2$ concentration as a function of said output signal.

9. The system of claim 8 wherein said laser has a sweep range centered at about 2.7082 μm.

10. The system of claim 9 wherein said processor is configured to normalize said output signal using a baseline established as a function of said zero absorption region and to determine said $CO_2$ concentration as a function of said normalized signal.

11. The system of claim 9 wherein said laser has a sweep range including substantially zero absorption regions on opposite sides of said $CO_2$ absorption features; and said processor is configured to normalize said output signal using a baseline established as a function of said zero absorption regions and to determine said $CO_2$ concentration as a function of said normalized signal.

12. The system of claim 9 wherein said laser has a sweep range from about 2.708 μm to about 2.7085 μm.

13. The system of claim 12 further including a plurality of modulating components, each of said modulating components being uniquely associated with a corresponding one of said plurality of probes, each of said modulating components being configured to introduce a unique modulation into said light beam passing through said corresponding probe.

14. The system of claim 13 wherein each of said modulating components is a wave chopper, each of said wave choppers configured to operate at a different chopping frequency.

15. The system of claim 14 wherein said processor is configured to discriminate between said plurality of light beams combined in said composite light beam based on said unique modulations.

16. The system of claim 6 further including a plurality of detectors, each of said detectors being uniquely associated with a corresponding one of said plurality of probes to provide an output signal representative of light intensity in a corresponding one of said light beams.

17. A method for determining concentration of a substance in a fluid stream, comprising the steps of:

providing a probe with a sampling chamber;

providing a swept-λ laser having a sweep range including a significant absorption feature of the substance and at least one substantially zero absorption region;

producing a light beam with the laser;

directing the light beam into said probe and through said sampling chamber, the sampling chamber containing the fluid stream to be measured;

receiving the light beam at a detector, the detector producing an output signal representative of light intensity in the light beam;

normalizing the output signal with a processor as a function of light intensity in the zero absorption region; and determining the concentration of the substance with a processor as function of the output signal of the detector, said normalizing step occurring prior said determining step.

18. The method of claim 17 further comprising the steps of:

providing a plurality of probes;

splitting the light beam into a plurality of split light beams;

directing each of the plurality of split light beams to a corresponding one of the plurality of probes;

providing a plurality of detectors;

receiving each of the plurality of split light beams at a corresponding one of the plurality of detectors; and separately determining the concentration of the substance at each of the plurality of probes with a processor as function of the output of the plurality of detectors.

19. The method of claim 17 further comprising the steps of:

providing a plurality of probes;

splitting the light beam into a plurality of split light beams;

introducing a different modulation into each of the split light beams;

directing each of the plurality of split light beams to a corresponding one of the plurality of probes;

combining the split light beams into a single composite light beam after said directing step;

providing a detector;

receiving the composite light beam at the detector, the detector providing an output signal; and separately determining the concentration of the substance at each of the plurality of probes with a processor as function of the output of the plurality of detectors, the processor discriminating between the plurality of probes as a function of the modulation introduced into each of the split light beams.

* * * * *